United States Patent
Denholm et al.

(10) Patent No.: US 7,468,370 B2
(45) Date of Patent: Dec. 23, 2008

(54) [1,7]NAPHTHYRIDINES AS PDE4 INHIBITORS

(75) Inventors: Alastair Denholm, Horsham (GB); Thomas Hugo Keller, Singapore (SG); Clive McCarthy, Basel (CH); Neil John Press, Horsham (GB); Roger John Taylor, Horsham (GB)

(73) Assignee: Novartis AG, Basel (CH)

( * ) Notice: Subject to any disclaimer, the term of this patent is extended or adjusted under 35 U.S.C. 154(b) by 329 days.

(21) Appl. No.: 10/538,355

(22) PCT Filed: Dec. 15, 2003

(86) PCT No.: PCT/EP03/14263

§ 371 (c)(1),
(2), (4) Date: Aug. 8, 2005

(87) PCT Pub. No.: WO2004/055013

PCT Pub. Date: Jul. 1, 2004

(65) Prior Publication Data

US 2006/0058338 A1    Mar. 16, 2006

(30) Foreign Application Priority Data

Dec. 16, 2002    (GB)    .................. 0229281.1

(51) Int. Cl.
C07D 471/02    (2006.01)
C07D 401/00    (2006.01)
A61K 31/497    (2006.01)
A61K 31/44    (2006.01)
A01N 43/42    (2006.01)

(52) U.S. Cl. .................. 514/253.04; 514/300; 546/122; 544/362

(58) Field of Classification Search .................. 546/122; 514/300, 253.04; 544/362
See application file for complete search history.

(56) References Cited

FOREIGN PATENT DOCUMENTS

| EP | 0 005 232 | 11/1979 |
|----|-----------|---------|
| WO | 98/18796  | * 5/1998 |

OTHER PUBLICATIONS

A. Nakata et al., Clinical and Experimental Immunology, 2002, vol. 128, pp. 460-466.*
Hersperger et al., "PD-Catalysed Cross-Coupling Reactions for the Synthesis of 6,8-Disubstituted 1.7-Naphtyridines: A Novel Class of Potent and Selective Phosphodiesterase Type 4D Inhibitors", J. Med. Chem., vol. 43, pp. 675-682 (2000).

* cited by examiner

Primary Examiner—D. Margaet Seaman
Assistant Examiner—Niloofar Rahmani

(57) ABSTRACT

Compounds of formula I

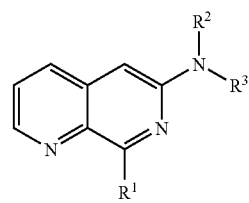

in free or salt form, wherein $R^1$, $R^2$ and $R^3$ have the meanings as indicated in the specification, are useful for treating conditions mediated by of phosphodiesterase type 4 or the down-regulation or inhibition of TNF-α release, particularly obstructive or inflammatory airways diseases. Pharmaceutical compositions that contain the compounds and processes for preparing the compounds are also described.

10 Claims, No Drawings

[1,7]NAPHTHYRIDINES AS PDE4 INHIBITORS

This invention relates to organic compounds, their preparation and their use as pharmaceuticals.

In one aspect, the present invention provides compounds of formula I

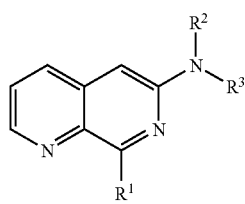

in free or salt form, where
$R^1$ is a monovalent aromatic group having up to 10 carbon atoms, and
$R^2$ and $R^3$ together with the nitrogen atom to which they are attached denote a heterocyclic group having up to 10 ring atoms and having 1 to 4 hetero atoms in the ring system.

"$C_1$-$C_8$-alkyl" as used herein denotes straight chain or branched $C_1$-$C_8$-alkyl, which may be, for example, methyl, ethyl, n-propyl, isopropyl, n-butyl, isobutyl, sec-butyl, tert-butyl, straight or branched pentyl, straight or branched hexyl, straight or branched heptyl, or straight or branched octyl. Preferably, $C_1$-$C_8$-alkyl is $C_1$-$C_4$-alkyl.

"$C_1$-$C_8$-alkylthio" as used herein denotes straight chain or branched $C_1$-$C_8$-alkyl substituted by thio, which may be, for example, methylthio, ethylthio, n-propylthio, isopropylthio, n-butylthio, isobutylthio, sec-butylthio, tert-butylthio, straight or branched pentylthio, straight or branched hexylthio, straight or branched heptylthio, or straight or branched octylthio. Preferably $C_1$-$C_8$-alkylthio is $C_1$-$C_4$-alkylthio.

"$C_1$-$C_8$-alkoxy" as used herein denotes straight chain or branched $C_1$-$C_8$-alkoxy which may be, for example, methoxy, ethoxy, n-propoxy, isopropoxy, n-butoxy, isobutoxy, sec-butoxy, tert-butoxy, straight or branched pentoxy, straight or branched hexyloxy, straight or branched heptyloxy, or straight or branched octyloxy. Preferably, $C_1$-$C_8$-alkoxy is $C_1$-$C_4$-alkoxy.

"Carboxy-$C_1$-$C_8$-alkoxy" as used herein denotes straight chain or branched $C_1$-$C_8$-alkoxy substituted in the alkyl by carboxy, which may be, for example, carboxy-methoxy, carboxy-ethoxy, carboxy-n-propoxy, carboxy-isopropoxy, carboxy-n-butoxy, carboxy-isobutoxy, carboxy-sec-butoxy, carboxy-tert-butoxy, straight or branched carboxy-pentoxy, straight or branched carboxy-hexyloxy, straight or branched carboxy-heptyloxy, or straight or branched carboxyoctyloxy. Preferably, carboxy-$C_1$-$C_8$-alkoxy is carboxy-$C_1$-$C_4$-alkoxy.

"$C_1$-$C_8$-haloalkyl" as used herein denotes $C_1$-$C_8$-alkyl as hereinbefore defined substituted by one or more halogen atoms, preferably one, two or three halogen atoms.

"$C_1$-$C_8$-haloalkoxy" as used herein denotes $C_1$-$C_8$-alkoxy as hereinbefore defined substituted by one or more halogen atoms, preferably one, two or three halogen atoms.

"Acyl" as used herein denotes alkylcarbonyl, for example $C_1$-$C_8$-alkylcarbonyl where $C_1$-$C_8$-alkyl may be one of the $C_1$-$C_8$-alkyl groups hereinbefore mentioned, optionally substituted by one or more halogen atoms; cycloalkylcarbonyl, for example $C_3$-$C_8$-cycloalkylcarbonyl where $C_3$-$C_8$-cycloalkyl may be, for example, cyclopropyl, cyclobutyl, cyclopentyl, cyclohexyl, cycloheptyl or cyclooctyl; 5- or 6-membered heterocyclylcarbonyl having one or two hetero atoms selected from nitrogen, oxygen and sulfur in the ring, such as furylcarbonyl, tetrahydrofurylcarbonyl, pyrrolidinylcarbonyl, piperidinylcarbonyl or pyridylcarbonyl; arylcarbonyl, for example $C_6$-$C_{10}$-arylcarbonyl such as benzoyl; or aralkylcarbonyl, for example $C_6$ to $C_{10}$-aryl-$C_1$-$C_4$-alkylcarbonyl such as benzylcarbonyl or phenylethylcarbonyl.

"$C_1$-$C_8$-alkoxycarbonyl" as used herein denotes $C_1$-$C_8$-alkoxy as hereinbefore defined linked through an oxygen atom thereof to a carbonyl group.

"$C_1$-$C_8$-haloalkoxycarbonyl" as used herein denotes $C_1$-$C_8$-haloalkoxy as hereinbefore defined linked through an oxygen atom thereof to a carbonyl group.

"$C_1$-$C_8$-hydroxyalkoxycarbonyl" and "$C_1$-$C_8$-alkoxy-$C_1$-$C_8$-alkoxycarbonyl" as used herein denote $C_1$-$C_8$-alkoxycarbonyl as hereinbefore defined in which the $C_1$-$C_8$-alkoxy group is substituted by hydroxy or a further $C_1$-$C_8$-alkoxy group respectively.

"Halogen" as used herein may be fluorine, chlorine, bromine or iodine; preferably it is fluorine, chlorine or bromine.

$R^1$ may be, for example, phenyl optionally substituted by one or more electron-withdrawing substituents, preferably selected from cyano, halogen, carboxy, aminocarbonyl, $C_1$-$C_8$-haloalkyl or $C_1$-$C_8$-haloalkoxy, preferably one or two such substituents, and/or optionally substituted by $C_1$-$C_8$-alkyl or $C_1$-$C_8$-alkoxy, or $R^1$ may be phenyl fused to another ring, for example a 3 to 8 membered heterocyclic ring having up to 4 carbon atoms, or $R^1$ may be a heterocyclic aromatic group having up to 10 ring atoms and 1 to 4 ring hetero atoms, preferably selected from nitrogen, oxygen and sulfur, for example a heterocyclyl group such as furyl, thienyl, pyrrolyl, imidazolyl, pyrazolyl, furazanyl, triazolyl, tetrazolyl, oxazolyl, isoxazolyl, thiazolyl, pyridyl, pyrimidyl, pyridazinyl, triazinyl, indolyl, isoindolyl or benzimidazolyl, which heterocyclyl group may be unsubstituted or substituted e.g. by at least one $C_1$-$C_8$-alkyl, halogen or $C_1$-$C_8$-alkoxy. Preferred groups $R^1$ include (a) phenyl substituted by cyano, halogen (particularly fluorine or chlorine), carboxy or $C_1$-$C_4$-haloalkoxy, and optionally by $C_1$-$C_4$-alkyl or $C_1$-$C_4$-alkoxy, (b) phenyl substituted by $C_1$-$C_4$-alkoxy and (c) an aromatic heterocyclic group having 5 or 6 ring atoms and one or two ring hetero atoms.

Heterocyclic groups denoted by $R^2$ and $R^3$ together with the nitrogen atom to which they are attached may be, for example, an optionally substituted azetidinyl, pyrrolidinyl, imidazolinyl, pyrazolidinyl, tetrahydrofurfuryl, piperidinyl, piperazinyl, morpholinyl, thiomorpholinyl, azacycloheptan-2-on-3-yl, indolinyl, isoindolinyl or benzimidazolinyl group. Preferably, it is a group having up to 6 ring atoms and one or two hetero atoms in the ring, which is preferably saturated, a second ring hetero atom where present preferably being nitrogen or oxygen. For example, the heterocyclic group may be a heterocyclyl, preferably saturated, group having up to 6, preferably 4, 5 or 6, ring atoms, and having one or two ring hetero atoms, preferably one or two nitrogen atoms or one nitrogen and one oxygen atom, optionally substituted by at least one substituent selected from $C_1$-$C_8$-alkyl, $C_1$-$C_8$-alkoxy, hydroxy, carboxy, acyl (preferably 5- or 6-membered heterocyclylcarbonyl having a nitrogen, oxygen or sulfur atom in the ring, especially 5-membered O-heterocyclylcarbonyl), aminocarbonyl, $C_1$-$C_8$-alkylaminocarbonyl, di-($C_1$-$C_8$-alkyl) aminocarbonyl, $C_1$-$C_8$-alkoxycarbonyl, $C_1$-$C_8$-haloalkoxycarbonyl, $C_1$-$C_8$-hydroxyalkoxycarbonyl, $C_1$-$C_8$-alkoxy-$C_1$-$C_8$-alkoxycarbonyl, $C_1$-$C_8$-alkylsulfonyl, or $C_1$-$C_8$-alkyl optionally substituted by hydroxy, cyano, carboxy or $C_1$-$C_8$-alkoxycarbonyl.

Preferred compounds of formula I in free or salt form include those where $R^1$ is phenyl substituted by one or two substituents selected from cyano, halogen, carboxy or $C_1$-$C_4$-haloalkoxy, and optionally by $C_1$-$C_4$-alkyl or $C_1$-$C_4$-alkoxy, or $R^1$ is phenyl substituted by $C_1$-$C_4$-alkoxy, and $R^2$ and $R^3$ together with the nitrogen atom to which they are attached denote a heterocyclic group having up to 6 ring atoms and one or two hetero atoms in the ring.

Further preferred compounds of formula I in free or salt form include those where $R^1$ is phenyl substituted by one or two substituents selected from cyano, halogen, carboxy or $C_1$-$C_4$-haloalkoxy meta to the indicated naphthyridine ring and optionally by $C_1$-$C_4$-alkyl or $C_1$-$C_4$-alkoxy ortho to the indicated naphthyridine ring, or $R^1$ is phenyl substituted by $C_1$-$C_4$-alkoxy meta to the indicated naphthyridine ring, and $R^2$ and $R^3$ together with the nitrogen atom to which they are attached denote a heterocyclyl group having up to 6 ring atoms and one or two nitrogen atoms, or one nitrogen atom and one oxygen atom, in the ring, optionally substituted by hydroxy, carboxy, 5-membered O-heterocyclylcarbonyl, aminocarbonyl, $C_1$-$C_4$-alkoxycarbonyl, $C_1$-$C_4$-alkylsulfonyl or $C_1$-$C_4$-alkyl optionally substituted by hydroxy, cyano, carboxy or $C_1$-$C_4$-alkoxycarbonyl.

Other preferred compounds of formula I in free or salt form include those where $R^1$ is phenyl optionally substituted by one, two or three substituents selected from the group consisting of cyano, $C_1$-$C_8$-alkyl, $C_1$-$C_8$-alkylthio, —SO—$C_1$-$C_8$-alkyl, and phenyl fused with a heterocyclic ring having 3 to 8 ring atoms of which up to 4 can be carbon atoms and up to 4 can be hetero atoms; and $R^2$ and $R^3$ together with the nitrogen atom to which they are attached denote a heterocyclic group having up to 6 ring atoms and one or two hetero atoms in the ring optionally substituted by carboxy, carboxy-$C_1$-$C_8$-alkoxy or $C_1$-$C_8$-alkoxycarbonyl-$C_1$-$C_8$-alkoxy, said heterocyclic group also optionally being substituted by $C_1$-$C_8$-alkyl, $C_1$-$C_8$-alkoxy.

Further preferred compounds of formula I in free or salt form include those where $R^1$ is phenyl optionally substituted by one, two or three substituents selected from the group consisting of cyano, $C_1$-$C_4$-alkyl, $C_1$-$C_4$-alkylthio, —SO—$C_1$-$C_4$-alkyl, and phenyl fused with a heterocyclic ring having 5 or 6 ring atoms of which up to 4 can be carbon atoms and up to 2 can be hetero atoms; and $R^2$ and $R^3$ together with the nitrogen atom to which they are attached denote a heterocyclic group having up to 6 ring atoms and one or two nitrogen atoms in the ring optionally substituted by carboxy, carboxy-$C_1$-$C_4$-alkoxy or $C_1$-$C_4$-alkoxycarbonyl-$C_1$-$C_4$-alkoxy, said heterocyclic group also optionally being substituted by $C_1$-$C_4$-alkyl.

The compounds represented by formula I are capable of forming acid addition salts, particularly pharmaceutically acceptable acid addition salts. Pharmaceutically acceptable acid addition salts of the compounds of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

Where $R^1$, or $R^2$ and $R^3$ together, contain an asymmetric carbon atom, the compounds of formula I in free or salt form exist in individual optically active isomeric forms or as mixtures thereof, e.g. as racemic or diastereomeric mixtures. The invention embraces both individual optically active R and S isomers as well as mixtures, e.g. racemic or diastereomeric mixtures, thereof.

Specific especially preferred compounds of formula I are those described hereinafter in the Examples.

The present invention also provides a process for the preparation of compounds of formula I in free or salt form which comprises (i) (A) reacting a compound of formula

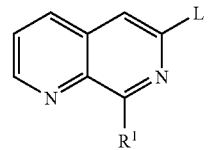

II optionally in protected form, where $R^1$ is as hereinbefore defined and L is a leaving atom or group, for example halogen or an aliphatic or aromatic sulfonyloxy group such as trifluoromethylsulfonyloxy, with a compound of formula

III optionally in protected form, where $R^2$ and $R^3$ are as hereinbefore defined, followed by deprotection if required;

(B) reacting a compound of formula I, where $R^2$ and $R^3$ together with the attached nitrogen atom denote a heterocyclyl group substituted by a $C_1$-$C_8$-alkoxycarbonyl group, to convert the alkoxycarbonyl group into a carboxy;

(C) for the preparation of compounds of formula I where $R^2$ and $R^3$ together with the attached nitrogen atom denote a heterocyclyl group substituted by carboxy-$C_1$-

$C_8$-alkoxy, hydrolysing a compound of formula I where $R^2$ and $R^3$ together with the attached nitrogen atom denote a heterocyclyl group substituted by $C_1$-$C_8$-alkoxycarbonyl-$C_1$-$C_8$-alkoxy; or (D) for the preparation of compounds of formula I when $R^1$ is phenyl substituted by —SO—$C_1$-$C_8$-alkyl, oxidising a compound of formula I where $R^1$ is phenyl substituted by $C_1$-$C_8$-alkylthio; and (ii) recovering the product in free or salt form.

Process variant (A) may be effected using known procedures for reaction of leaving atoms or groups with amines or analogously, for example as hereinafter described in the Examples. Where it is desired to minimise the possibility of reaction of functional groups other than those participating in the desired reaction, such functional groups may be protected by conventional protecting groups. For example, where $R^2$ and $R^3$ together in the compound of formula III contain an amino group it may be protected by a protecting group such as tert-butoxycarbonyl, which can be removed after the reaction of II and III by a conventional deprotection reaction.

Process variant (B) may be effected using known procedures for conversion of alkoxycarbonyl groups to carboxy groups, e.g. hydrolysis with an aqueous alkali metal hydroxide, or analogously such as hereinafter described in the Examples.

Process variant (C) may be effected using art known procedures for the hydrolysis of esters to carboxylic acids, e.g. using trifluoroacetic acid, or analogously such as hereinafter described in the Examples.

Process variant (D) may be effected using art known procedures for the oxidation of sulfinyl groups to sulfinyl groups, e.g. using hydrogen peroxide or ozone, or analogously such as hereinafter described in the Examples.

Compounds of formula II may be prepared as described in WO98/18796 or analogously. Compounds of formula III are commercially available or may be prepared by known procedures.

Where reference is made herein to protected functional groups or to protecting groups, the protecting groups may be chosen in accordance with the nature of the functional group, for example as described in Protective Groups in Organic Synthesis, T. W. Greene and P. G. M. Wuts, John Wiley & Sons Inc, Second Edition, 1991, which reference also describes procedures suitable for replacement of the protecting groups by hydrogen.

Compounds of formula I in free or salt form are useful as pharmaceuticals. Accordingly the invention also provides a compound of formula I in free or salt form for use as a pharmaceutical. The compounds of formula I in free or salt form, hereinafter referred to alternatively as "AGENTS OF THE INVENTION", exhibit cyclic nucleotide phosphodiesterase (PDE) isoenzyme inhibiting activity, selective for type 4 isoenzyme. AGENTS OF THE INVENTION possess anti-inflammatory, anti-airways hyperreactivity and bronchodilator properties. They further possess immunosuppressive and TNFα secretion inhibitory activities. The pharmacological activities may be demonstrated in test methods, for example as follows:

PDE4 Isoenzyme Inhibition Assay

Cloning: GATEWAY flanked PDE4 cDNA constructs containing the coding regions of the three isoenzymes, human PDE4A, human PDE4B, and human PDE4D are generated by PCR and transposed into the GATEWAY shuttle vector pDO-NOR-201. In addition a 6-histidine tag is introduced by PCR onto the carboxyl terminal end of each of the constructs to facilitate protein purification. Following sequence verification, the PDE4 constructs are transposed into the GATEWAY expression vector pDEST-8. Positive recombinants are selected and transposed into E. coli strain DH10Bac and bacmid produced transfected into SF21 cells using Bac-To-Bac (Invitrogen Life Technologies). Positive transfections are selected and used to generate high titer viral stocks for use in protein expression.

PDE4 Expression: Sf21 cells are grown to a density of 2×106 cells/ml and infected with human PDE4A, PDE4B or PDE4D3 containing baculovirus to a multiplicity of infection (m.o.i.) of 1 for 72 hours. The infected cells are harvested by centrifugation at 1,400 g for 4 minutes at 4° C. and the cell pellets are frozen at −80° C. Sf21 (Spodoptera frugiperda 21) insect cells are routinely maintained at densities between 3×105 and 3×106 cells/ml in SF00 Serum Free Medium (Invitorgen Life Technologies). Sf21 cells (1×109) are resuspended in 100 ml cold (4° C.) Lysis Buffer (50 mM $Na_2HPO4$, 200 mM NaCl, 10 mM Imidazole). Cells are incubated on ice for 30 minutes then centrifuged at 15,000 g for 20 minutes at 4° C.

PDE4 Purification: The 6 Histidine-tagged PDE4 proteins are isolated from crude cell lysates by a batch-wise Ni-NTA purification strategy (QIAGEN). N-NTA resin is first pre-rinsed to remove ethanol preservative and equilibrated with Lysis Buffer. Cell lysate is added, (10 ml 50% Ni-NTA slurry resin per 50 ml lysate), and gently rotated on a mixer at 4° C. for 1-2 h. The sample is then centrifuged at 1,000 g for 5 minutes at 4° C. using Denley benchtop centrifuge. The supernatant is removed and the resin is washed 3 times with 50 ml ice cold Wash Buffer (50 mM $Na_2HPO4$, 300 mM NaCl and 20 mM imidazole) followed by centrifugation at 1,000 g for 5 minutes at 4° C. The 6His-tagged protein is eluted from the resin with 3×5 ml ice cold Elution Buffer (50 mM $NaH2PO4$, 300 mM NaCl, 250 mM imidazole) and collected by centrifugation at 1,000 g for 5 minutes at 4° C. The supernatants are then pooled before buffer exchange and concentration using a VivaScience 20 ml 5K 0.2 μM Concentrator. Samples are aliquoted and stored at −20° C.

SDS-PAGE Electrophoresis: Purified PDE4 samples are analysed by SDS-PAGE using 8-16% gradient mini-gels (Novex) and samples are denatured at 100° C. in reducing sample buffer (62 mM Tris-HCl pH 6.8, 10% glycerol, 3% SDS, 5% β-mercaptoethanol, 0.02% bromophenol blue) for 3 min prior to loading. Novex SeeBlue pre-stained MW standards are also loaded. Gels are run at a constant 25 mA. Gels are stained with GelCode Colloidal Coomassie G-250 Blue Stain Reagent (Pierce) according to the manufacturer's procedure.

Western Blot Analysis: Samples are analysed on Novex 8-16% gradient gels as described above. The gel is then wet blotted onto Millipore Immobilon-P PVDF membrane using the tank transfer method with 25 mM Tris-HCl pH 8.8, 192 mM Glycine, 15% methanol transfer buffer at 80 mA for 16 hours. Immunoprobing is carried out in TTBS buffer (20 mM Tris-HCl pH 7.6, 0.9% (w/v) NaCl, 0.05% (v/v) Triton X-100, 0.5% (w/v) casein) with an anti-6his monoclonal antibody (QIAGEN) at 1:1000 dilution, An anti-mouse IgG alkaline phosphatase conjugate is used as the secondary antibody (Sigma A9919) at 1:10000 dilution and proteins visualised with BCIP/NBT substrate prepared from tablets (Sigma) according to the manufacturers procedure.

PDE4 Assay: The assay is based on Amersham Pharmacia Biotech Scintillation Proximity Assay (SPA) technology. Enzyme is diluted with enzyme dilution buffer (10 mM Tris-HCl, pH 7.5 containing 1 mM EDTA) in order to obtain between 10-30% total substrate hydrolysis during the assay. The enzymatic reaction is started by adding 10 μl diluted enzyme to 80 μl substrate (0.1 μCi [3H]-cAMP, 1 μM cAMP) and 10 μl inhibitor solution in a 96-well microtiter plate. After 30-60 minutes incubation at room temperature the reaction is stopped by adding 50 μl PDE SPA beads (20 mg/ml). After 30 minutes the plate is centrifuged (3000 g, 10 minutes) and counted (Packard TopCount).

Inhibitor stock solutions are prepared in 100% dimethyl-sulphoxide (DMSO) and diluted with DMSO/water to achieve 10 concentrations to cover the range of 0-100% inhibition. The concentration of DMSO is kept constant at 1% (v/v) throughout the assay. The concentration at which 50% inhibition occurs ($IC_{50}$) is determined from inhibition—concentration curves in a conventional manner. Within the PDE4 isoenzyme group, AGENTS OF THE INVENTION generally exhibit selectivity for inhibition of PDE4D isoenzyme relative to PDE4A, PDE4B and PDE4C. The compounds of Examples 1, 3, 12, 15, 37 and 39 have $IC_{50}$ values of 1 nM, 3.1 nM, 2.5 nM, 10.4 nM, 14.0 nM and 8.0 nM respectively for inhibition of PDE4D in the above assay.

Having regard to their inhibition of binding of PDE4, agents of the invention are useful in the treatment of conditions mediated by PDE4, particularly inflammatory conditions. Treatment in accordance with the invention may be symptomatic or prophylactic.

Accordingly, AGENTS OF THE INVENTION are useful in the treatment of inflammatory or obstructive airways diseases, resulting, for example, in reduction of tissue damage, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial or viral infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, their influence on airways hyperreactivity and their profile in relation to PDE isoenzyme inhibition, in particular as selective type 4 inhibitors, AGENTS OF THE INVENTION are useful for the treatment, in particular prophylactic treatment, of obstructive or inflammatory airways disease. Thus by continued and regular administration over prolonged periods of time AGENTS OF THE INVENTION are useful in providing advance protection against recurrence of bronchoconstrictor or other symptomatic attack consequential to obstructive or inflammatory airways disease or for the control, amelioration or reversal of basal status of such disease.

Having regard to their bronchodilator activity AGENTS OF THE INVENTION are useful as bronchodilators, e.g. for the treatment of chronic or acute broncho-constriction, e.g. for the symptomatic treatment of obstructive or inflammatory airways disease. Having regard to their activity as selective inhibitors of TNF-α release, AGENTS OF THE INVENTION are also useful for the down-regulation or inhibition of TNF-α release, e.g. for the treatment of diseases or conditions in which TNF-α release is implicated or plays a mediating role, e.g. diseases or conditions having an aetiology involving or comprising morbid, for example undesirable, excessive or unregulated TNF-α release, in particular for the treatment of cachexia or endotoxin shock and in treatment of AIDS [cf. Sharief et al, Mediators of Inflammation, 1 323-338 (1992)], the treatment of cachexia associated with morbid TNF-α release or TNF-α blood-serum levels of whatever origin, including cachexia consequential to, e.g. bacterial, viral or parasitic, infection or to deprivation or deterioration of humoral or other organic, e.g. renal function, the treatment of cancerous, malarial and vermal cachexia, cachexia resulting from dysfunction of the pituitary, thyroid or thymus glands as well as uremic cachexia and, in particular, the treatment of AIDS-related cachexia, i.e. cachexia consequential to or associated with to HIV infection.

The method of the invention is also applicable to the treatment of septic shock, e.g., shock conditions resulting from bacterial infection. In this regard it is to be noted that the present invention provides a method for the treatment of septic shock as such as well as of conditions consequential to or symptomatic of septic or shock, for example ARDS.

The AGENTS OF THE INVENTION are further applicable to the treatment of disease consequential to HIV infection, e.g. AIDS, e.g. to the amelioration or control of the advance of such disease.

Having regard to their profile in relation to inhibition of PDE isoenzymes and/or TNF-α release inhibition, as well as their immunosuppressive activity, AGENTS OF THE INVENTION are also useful as immunosuppressive agents, e.g. for the treatment of autoimmune diseases, in particular for the treatment of autoimmune diseases in which inflammatory processes are implicated or which have an inflammatory component or aetiology, or as anti-inflammatory agents for the treatment of inflammatory disease in particular for the treatment of inflammatory disease in which autoimmune reactions are implicated or which have an autoimmune component or aetiology. Examples of such disease to which the present invention is applicable include autoimmune haematological disorders (e.g. haemolytic anaemia, aplastic anaemia, pure red cell anaemia and idiopathic thrombocytopenia), systemic lupus erythematosus, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy), as well as inflammatory and/or hyperproliferative skin diseases such as psoriasis, atopic dermatitis, pemphigus and, in particular, contact dermatitis, e.g. allergic contact dermatitis.

AGENTS OF THE INVENTION are in particular useful for the treatment of arthritis, and other rheumatic or inflammatory disease, especially for the treatment of rheumatoid arthritis. As immunosuppressants AGENTS OF THE INVENTION are further useful in the prevention of graft rejection, e.g. for the maintenance of allogenic organ transplants or the like, e.g. in relation to kidney, liver, lung, heart, heart-lung, bowel, bone-marrow, skin, or corneal transplant.

Having regard to their profile in relation to inhibition of PDE isoenzymes, in particular their profile as selective type 4 inhibitors, AGENTS OF THE INVENTION are further useful for the treatment of disease involving tissue calcium depletion, in particular degenerative diseases of the bone and joint involving calcium depletion, especially osteoporosis. In this regard they are further useful for the treatment of allergic inflammatory diseases such as rhinitis, conjunctivitis, atopic dermatitis, urticaria and gastro-intestinal allergies; as vasodilators, e.g. for the treatment of angina, hypertension, ischaemia/reperfusion injury, congestive heart failure and multi-infarct dementia; and for the treatment of other conditions where inhibition of PDE 4 is indicated, for example, depression, conditions and diseases characterised by impaired cognitive function including Alzheimer's disease, Parkinson's disease and stroke.

The AGENTS OF THE INVENTION are also useful as co-therapeutic agents in combination with other drug substances such as anti-inflammatory, bronchodilatory, antihistamine or immunosuppressive drug substances, particularly in the treatment of inflammatory diseases e.g. obstructive or inflammatory airways diseases, autoimmune diseases or graft rejection such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Such anti-inflammatory drugs include steroids, in particular glucocorticosteroids such as budesonide, beclamethasone, fluticasone, ciclesonide or mometasone, LTB4 antagonists such as those described in U.S. Pat. No. 5,451,700 and LTD4 antagonists such as montelukast and zafirlukast, dopamine receptor agonists such as cabergoline, bromocriptine, ropinirole and 4-hydroxy-7-[2-[[2-[[3-(2-phenylethoxy)propyl]-sulfonyl]ethyl]-amino]ethyl]-2(3H)-benzothiazolone and pharmaceutically acceptable salts thereof (the hydrochloride being Viozan®—AstraZeneca).

Such bronchodilatory drugs include anticholinergic or antimuscarinic agents, in particular ipratropium bromide, oxitropium bromide and tiotropium bromide, and beta-2 adrenoceptor agonists such as salbutamol, terbutaline, salmeterol and, especially, formoterol and pharmaceutically acceptable salts thereof, and compounds (in free or salt or solvate form) of formula I of PCT International Publication No. WO 00/75114, which document is incorporated herein by reference, preferably compounds of the Examples thereof, especially a compound of formula

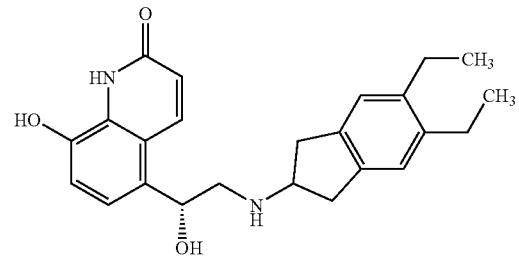

and pharmaceutically acceptable salts thereof. Co-therapeutic antihistamine drug substances include cetirizine hydrochloride, acetaminophen, clemastine fumarate, promethazine, loratidine, desloratidine, diphenhydramine and fexofenadine hydrochloride. Co-therapeutic immunosuppressive drug substances include, e.g. cyclopeptide, cyclopeptolide or macrolide drug substances, for examples drugs belonging to the cyclosporin class, e.g. cyclosporins A or G, the drug substances tacrolimus (also known as FK 506), ascomycin and rapamycin and their various known congeners and derivatives.

Combinations of agents of the invention and steroids, beta-2 agonists, or LTD4 antagonists may be used, for example, in the treatment of COPD or, particularly, asthma. Combinations of agents of the invention and anticholinergic or antimuscarinic agents, PDE4 inhibitors, dopamine receptor agonists or LTB4 antagonists may be used, for example, in the treatment of asthma or, particularly, COPD. Combinations of agents of the invention and immunosuppressive drug substances may be used in the treatment of any disease or condition requiring immunosuppressive treatment as hereinbefore described.

Other useful co-therapeutic combinations of AGENTS OF THE INVENTION include combinations with PDE3 inhibitors such as those disclosed in WO 00/66123, e.g. revizinone, ci-lostamide, amipizone, siguazodan, carbazeran, bemoradan, motapizone and, particularly, milrinone, enoximone and pimopendan, especially for treatment of conditions characterised by acute or chronic obstruction of vessels and/or bronchi and/or acute or chronic inflammation, e.g. acute obstructive bronchitis, bronchial asthma or COPD. In accordance with the foregoing, the present invention also provides a method for the treatment of a disease mediated by PDE4 which comprises administering to a subject, particularly a human subject, in need thereof an effective amount a compound of formula I, or a pharmaceutically acceptable salt thereof, as hereinbefore described. In another aspect, the invention provides a compound of formula I, or a pharmaceutically acceptable salt thereof, as hereinbefore described for use in the preparation of a medicament for the treatment of a disease mediated by PDE4.

In accordance with the foregoing, the present invention also provides a method for the treatment of an inflammatory disease, particularly an obstructive or inflammatory airways disease, which comprises administering to a subject, particularly a human subject, in need thereof an effective amount a compound of formula I, or a pharmaceutically acceptable salt thereof, as hereinbefore described. In another aspect, the invention provides a compound of formula I, or a pharmaceutically acceptable salt thereof, as hereinbefore described for use in the preparation of a medicament for the treatment of an inflammatory disease, particularly an obstructive or inflammatory airways disease.

The agents of the invention may be administered by any appropriate route, e.g. orally, for example in the form of a tablet or capsule; parenterally, for example intravenously; topically to the skin, for example in the treatment of psoriasis; intranasally, for example in the treatment of rhinitis; or by inhalation, particularly in the treatment of obstructive or inflammatory airways diseases.

In a further aspect, the invention also provides a pharmaceutical composition comprising as active ingredient a compound of formula I in free form or in the form of a pharmaceutically acceptable salt thereof, optionally together with a pharmaceutically acceptable diluent or carrier therefor. Such compositions may be prepared using conventional diluents or excipients and techniques known in the galenic art. Thus oral dosage forms may include tablets, capsules and controlled release formulations such as encapsulated or matrix dissolution formulations, osmotic system formulations or ion exchange resin formulations. Formulations for topical administration may take the form of creams, ointments, gels or transdermal delivery systems, e.g. patches. Compositions for inhalation may comprise aerosol or other atomizable formulations, or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention also includes (A) a compound of formula I as hereinbefore described in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages employed in practising the invention will of course vary depending, for example, on the particular condition to be treated, the effect desired and the mode of administration. In general, suitable daily dosages for oral administration are of the order of 0.5 to 200 mg, while suitable daily dosages for administration by inhalation are of the order of from 0.1 to 10 mg.

The invention is illustrated by the following Examples. 6-Amino-8-bromo-1,7-naphthyridine used in the Examples is prepared as described in WO98/18796.

EXAMPLE 1

3-[6-(3-Hydroxy-pyrrolidin-1-yl)-[1,7]naphthyridin-8-yl]-benzonitrile 6-amino-8-(3-cyanophenyl)-1,7-naphthyridine To a mixture of THF (80 ml) and 2N sodium carbonate (34 ml, aqueous) is added 6-amino-8-bromo-1,7-naphthyridine (4.007 g), triphenylphosphine (0.37 g) and 3-cyanophenyl-boronic acid (3.23 g). The mixture is degassed under argon three times and then bis(di-benzylidene-acetone)palladium (0) (0.4 g) is added and the mixture is degassed under argon three more times. The mixture is heated at 80° C. under argon for 16 hours then cooled and filtered. The mixture is diluted with ethyl acetate and washed with 2N sodium hydroxide then brine. After drying over sodium sulfate the organic layer is evaporated and suspended in ether. The solid precipitate thus obtained is the title compound, which is filtered off.
M.p. 182-184° C. HRMS $[M+H]^{+\,found}$=247.1

6-Trifluromethanesulfonyl-8-(3-cyanophenyl)-1,7-naphthyridine—Compound A

To a solution of 6-amino-8-(3-cyanophenyl)-1,7-naphthyridine (4.058 g) in dimethyl-formamide (DMF) (22 ml) under argon at 0° C. is added trifluoromethanesulfonic acid (11 ml). The mixture is stirred at 0° C. for 10 minutes and then sodium nitrite (2.26 g) is added slowly. The cooling bath is then removed and the mixture stirred at room temperature for 3 hours. The resulting mixture is diluted with ethyl acetate and washed with water, 2M NaOH and water again. The organic layer is dried over sodium sulfate, then concentrated in vacuo and purified by column chromatography, eluting with 10:0.5 toluene:acetone to yield the title compound. M.p. 102-104° C. MS (m/e)=380.

3-[6-(3 Hydroxy-pyrrolidin-1-yl)-[1,7]naphthyridin-8-yl]-benzonitrile

Compound A (201 mg) is dissolved in DMSO (1.2 ml) with 3-pyrrolidinol (0.1 ml) and the mixture heated at 60° C. for 2 days or until complete by high performance liquid chromatography (HPLC). After cooling, ethyl acetate is added to the mixture, which is washed four times with brine. The organic layer is dried over sodium sulfate and concentrated. Purification by column chromatography eluting with 25% ethyl acetate in hexane yields 3-[6-(3-hydroxy-pyrrolidin-1-yl)-[1,7]naphthyridin-8-yl]-benzonitrile. M.p.=132-133° C. TOF M.S. (ES+) 317.

EXAMPLE 2

3-{6-[4(2-Cyano-ethyl)-piperazin-1-yl]-[1,7]naphthyridin-8-yl}-benzonitrile

Compound A (202 mg) is dissolved in DMSO (1.2 ml) with 3-(1-piperazinyl)-proprionitrile (171 mg) and the mixture heated at 60° C. until complete by HPLC (2 days). After cooling, ethyl acetate is added to the mixture, which is washed four times with brine. The organic layer is dried over sodium sulfate and concentrated. Purification by column chromatography eluting with 25% ethyl acetate in hexane yields 3-{6-[4-(2-cyano-ethyl)-piperazin-1-yl]-[1,7]naphthyridin-8-yl}-benzonitrile. The product is isolated as the hydrochloride salt by dissolving in dioxane (5 mL) and adding 4 M HCl in dioxane (0.07 ml). The resultant precipitate is filtered and washed with dioxane. M.p.>200° C., TOF M.S. (ES+) 369.

EXAMPLE 3

1-[8-(3-Cyano-phenyl)-[1,7]naphthyridin-6-yl]-piperidine-4-carboxylic acid, Lithium salt Compound B: 1-[8-(3-Cyano-phenyl)-[1,7]naphthyridin-6-yl]-piperidine-4-carboxylic acid ethyl ester Compound A (286 mg) is dissolved in DMSO (2 ml) with piperidine-4-carboxylic acid ethyl ester (271 mg), and the mixture heated at 60° C. until reaction is complete by HPLC (2 days). After cooling, ethyl acetate is added to the mixture, which is washed four times with brine. The organic layer is dried over sodium sulfate and concentrated. Purification by column chromatography eluting with 25% ethyl acetate in hexane yields 1-[8-(3-cyano-phenyl)-[1,7]naphthyridin-6-yl]-piperidine-4-carboxylic acid ethyl ester. HPLC (3 min, 30% formic acid/water to 95% formic acid/water) retention time=1.98 minutes. TOF M.S. (ES+) 387.

1-[8-(3-Cyano-phenyl)-[1,7]naphthyridin-6-yl]-piperidine-4-carboxylic add, Lithium salt Compound B (234 mg) is dissolved in TIF (5.8 ml) and a 1M aqueous solution of lithium hydroxide (785 μl) is added. The mixture is stirred at room temperature until reaction is complete by HPLC (48 hours). Ethyl acetate is then added to the mixture slowly until a solid precipitate appears. This precipitate is filtered, washed with ethyl acetate and dried in vacuo. 1-[8-(3-Cyano-phenyl)-[1,7]naphthyridin-6-yl]-piperidine-4-carboxylic acid, lithium salt is obtained as a yellow solid. M.p.>200° C. TOF M.S. (ES+) 359.

EXAMPLE 4

3-(6-Piperazin-1-yl-[1,7]naphthyridin-8-yl)-benzonitrile

Compound C: 4-[8-(3-Cyano-phenyl)-[1,7]naphthyridin-6-yl]-piperazine-1-carboxylic acid tert-butyl ester Compound A (250 mg) is dissolved in DMSO (2 ml) with piperazine-1-carboxylic acid tert-butyl ester (283 mg), and the mixture heated at 60° C. for 2 days or until reaction is complete by HPLC. After cooling, ethyl acetate is added to the mixture, which is washed four times with brine. The organic layer is dried over sodium sulfate and concentrated. Purification by column chromatography eluting with 25% ethyl acetate in hexane yields 4-[8-(3-cyano-phenyl)-[1,7]naphthyridin-6-yl]-piperazine-1-carboxylic acid tert-butyl ester. HPLC (3 minutes, 30% formic acid/water to 95% formic acid/water) retention time=2.03 minutes.
TOF M.S. (ES+) 416.

3-(6-Piperazin-1-yl-[1,7]naphthyridin-8-yl)-benzonitrile

Compound C (210 mg) is dissolved in dioxane (2 ml) and 4M HCl in dioxane (1 ml) is added dropwise. The mixture is stirred at room temperature for 24 h, after which the solid precipitate is filtered and washed with ethyl acetate. The solid is dried in vacuo to yield 3-(6-piperazin-1-yl-[1,7]naphthyridin-8-yl)-benzonitrile as the hydrochloride. M.p.>250° C. TOF M.S. (ES+) 316.

EXAMPLES 5 TO 21

By analogous procedures to the appropriate Examples above and using appropriate starting materials together with Compound A, the following compounds of formula I are obtained as identified in Table 1 together with mass spectrometry characterising data (TOFMS(ES+)). The compounds are obtained in free form, except Examples 16 and 19 which are obtained as the lithium and hydrochloride salts respectively.

TABLE 1

| Ex. | $R^1$ | $NR^2R^3$ | MS |
|---|---|---|---|
| 5 | 3-cyanophenyl | 1-methylpiperidin-4-yl carboxamide | 358 |
| 6 | 3-cyanophenyl | 1-methyl-4-hydroxypiperidinyl | 331 |
| 7 | 3-cyanophenyl | 1-methyl-4-(hydroxymethyl)piperidinyl | 345 |
| 8 | 3-cyanophenyl | 1-methyl-4-(2-hydroxyethyl)piperidinyl | 359 |
| 9 | 3-cyanophenyl | 1-methyl-2-(hydroxymethyl)pyrrolidinyl | 330 |
| 10 | 3-cyanophenyl | 1-methyl-4-(tetrahydrofuran-2-ylcarbonyl)piperazinyl | 414 |

TABLE 1-continued

| Ex. | R¹ | NR²R³ | MS |
|---|---|---|---|
| 11 | 3-cyanophenyl | 1-methylpiperidine-3-carboxamide | 358 |
| 12 | 3-cyanophenyl | 4-methylmorpholine | 317 |
| 13 | 3-cyanophenyl | 1-methylpyrrolidine-2-carboxamide | 344 |
| 14 | 3-cyanophenyl | 1-methylpyrrolidine-2-carboxylic acid | 345 |
| 15 | 3-cyanophenyl | 1-methyl-4-methylpiperazine | 330 |
| 16 | 3-cyanophenyl | (4-methylpiperazin-1-yl)acetic acid | 374 |
| 17 | 3-cyanophenyl | ethyl (piperazin-1-yl)acetate | 401 |
| 18 | 3-cyanophenyl | 1-methyl-4-(methylsulfonyl)piperazine | 394 |
| 19 | 3-cyanophenyl | 2,5-dimethyl-1-methylpiperazine | 344 |
| 20 | 3-cyanophenyl | 1-methyl-4-ethylpiperazine | 344 |
| 21 | 3-cyanophenyl | 1-methylazetidine-3-carboxylic acid | 331 |

EXAMPLE 22

1-[8-(3-Fluoro-phenyl)-[1,7]naphthyridin-6-yl]-piperidine-4-carboxylic acid ethyl ester 8-(3-Fluoro-phenyl)-[1,7]naphthyridin-6-ylamine—Compound D To a stirred solution of 6-amino-8-bromo-1,7-naphthyridine (0.5 g) in a mixture of toluene (2.5 ml), DMF (4 ml) and aqueous $K_2CO_3$ (0.68 g in 2 ml water) is added bis(dibenzylideneacetone)palladium (51 mg), triphenylphosphine (47 mg) and 3-fluorphenylboronic acid (0.33 g). The mixture is stirred for 4 hours at 100° C. The mixture is diluted with ethyl acetate, then filtered through a Celite™ filter. The ethyl acetate solution is washed with 2 N NaOH and water, dried over magnesium sulphate, then concentrated to afford the title compound. MS: APCI 240.0 MH⁺.

Trifluromethanesulfonic acid 8-(3-fluorophenyl)-[1,7]naphthyridin-6-yl ester—Compound E Trifluoromethanesulfonic acid (5 ml) is added dropwise to a solution of Compound D (0.5g) in DMF (10 ml) at below 0° C. After warming the mixture to room temperature, sodium nitrate (0.3 g) is added slowly. The mixture is stirred at room temperature for 3 hours, then diluted with ethyl acetate and washed with water, 2 M sodium carbonate and water again. The organic layer is dried over magnesium sulfate, then concentrated in vacuo. Purification by column chromatography, eluting with ethyl acetate/hexane (1:4), gives the title compound. MS: APCI 372.9 MH⁺.

1-[8-(3-Fluoro-phenyl)-[1,7]naphthyridin-6yl]-piperidine-4-carboxylic acid ethyl ester A solution of Compound E (160 mg) and piperidine-4-carboxylic acid ethyl ester (149 mg) in DMSO (1 ml) is heated at 60° C. for 72 hours. After cooling, ethyl acetate is added to the mixture, which is then washed with water and three times with brine. The organic layer is dried over magnesium sulfate and concentrated. Purification by column chromatography eluting with 25% ethyl acetate in iso-hexane yielded the product. MS: APCI 380.0 MH+.

EXAMPLE 23

Sodium 1-[8-(3-fluoro-phenyl)-[1,7]naphthyridin-6-yl]-piperidine-4-carboxylate

Sodium hydroxide (1 M, 0.25 ml) is added to a solution of 1-[8-(3-fluoro-phenyl)-[1,7]naphthyridin-6-yl]-piperidine-4-carboxylic acid ethyl ester (96 mg, 0.25 mmol) in THF (1 ml). The solution is stirred at room temperature for 24 hours, then heated to 45° C. for 24 hours. Water and ethyl acetate are added and the aqueous phase separated and evaporated to give the title compound. MS: APCI 352.0 MH+.

EXAMPLE 24

1-[8-(5-Fluoro-2-methoxy-phenyl)-[1,7]naphthyridin-6-yl]-piperidine-4-carboxylic acid ethyl ester 8-(5-Fluoro-2-methoxy-phenyl)-[1,7]naphthyridin-6-ylamine—Compound F To a stirred solution of 8-bromo-[1,7]naphthyridin-6-ylamine (1.70 g) in a mixture of toluene (7 ml), DMF (11 ml) and aqueous $K_2CO_3$ (2.31 g in 5 ml water) is added bis(dibenzylideneacetone)palladium (174 mg), triphenylphosphine (158 mg) and 5-fluoro-2-methoxyphenylboronic acid (1.38 g). The mixture is stirred for 3.5 hours at 100° C., then diluted with ethyl acetate and filtered through Celite. The ethyl acetate solution is washed with 2N NaOH and water, dried over magnesium sulphate, then concentrated to afford the title compound. MS: APCI 270.0 MH+.

Trifluoro-methanesulfonic acid 8-(5-fluoro-2-methoxy-phenyl)-[1,7]naphthyridin-6-yl ester—Compound G Trifluoromethanesulfonic acid (9 ml) is added dropwise to a solution of Compound F (2.0 g) in DMF (15 ml) at below 0° C. The mixture is warmed to 10° C., then sodium nitrite (1.04 g) is added slowly. The mixture obtained is stirred at room temperature for 2.5 hours, then diluted with ethyl acetate and washed with water, 2M sodium carbonate and water again. The organic layer is dried over magnesium sulfate then concentrated in vacuo. Purification by column chromatography, eluting with ethyl acetate/hexane (1:1), gives the title compound.
MS: APCI 402.9 MH+.

1-[8(5-Fluoro-2-methoxy-phenyl)-[1,7]naphthyridin-6-yl]piperidine-4-carboxylic acid ethyl ester A solution of Compound G (200 mg) and piperidine-4-carboxylic acid ethyl ester (0.17 ml) in DMSO (1.5 ml) is heated at 60° C. for 70 hours. After cooling, ethyl acetate is added to the mixture, which is then washed six times with water and then with brine. The organic layer is dried over magnesium sulfate and concentrated. Ether is added to the mixture and the resulting solid filtered off. The residue is purified by silica gel chromatography, eluting with 50% ethyl acetate in iso-hexane yielded the product. MS: APCI 410.1 MH+.

EXAMPLE 25

Potassium 1-[8-(5-fluoro-2-methoxy-phenyl)-[1,7] naphthyridin-6-yl]-piperidine-4-carboxylate Sodium hydroxide (2 M, 0.1 ml) is added to a solution 1-[8-(5-Fluoro-2-methoxy-phenyl)-[1,7]naphthyridin-6-yl]-piperidine-4-carboxylic acid ethyl ester (67 mg, 0.16 mmol) in MeOH/THF (1:1, 4 ml). The solution is stirred at room temperature for 48 hours. Water and ethyl acetate are added. The aqueous phase is separated and acidified to pH 4.5, then extracted with ethyl acetate three times. The ethyl acetate extract is washed with water, brine and dried over magnesium sulphate before evaporation to give the free acid. A solution of potassium carbonate (8.5 mg) and the above acid in methanol is evaporated to give the title compound. MS: APCI 382.0 MH+.

EXAMPLES 26 TO 33

By procedures analogous to the appropriate Examples above, and using appropriate starting materials, compounds of formula I are obtained as identified in Table 2 together with mass spectrometry characterising data (MS:APCI MH+). The compounds are obtained in free form, except Examples 29, 32 and 33, which are obtained as the sodium salts.

TABLE 2

| Ex. | $R^1$ | $R^2$ | MS |
|---|---|---|---|
| 26 | 3-chlorophenyl | N-methylpiperidine-4-carboxylic acid ethyl ester | 396.0 |
| 27 | 2-methoxy-4-chlorophenyl | N-methylpiperidine-4-carboxylic acid ethyl ester | 425.9 |
| 28 | 3-carboxyphenyl | N-methylmorpholine | 336.0 |
| 29 | 3-chlorophenyl | N-methylpiperidine-4-carboxylic acid | 368.0 |
| 30 | 3-chlorophenyl | N-methylpiperidine-3-carboxylic acid ethyl ester | 396.0 |

TABLE 2-continued

| Ex. | R¹ | R² | MS |
|---|---|---|---|
| 31 | 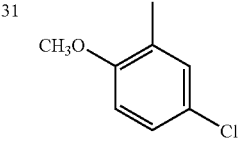 | 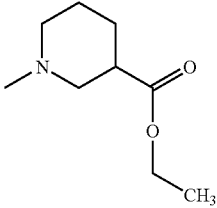 | 410.1 |
| 32 | 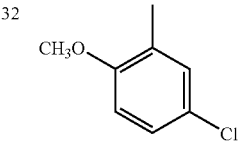 | 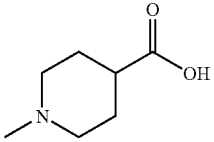 | 398.0 |
| 33 | 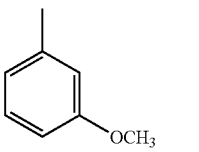 | 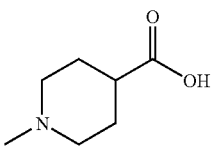 | |

EXAMPLES 34 TO 44

By procedures analogous to the appropriate Examples above, and using appropriate starting materials, compounds of formula I are obtained as identified in Table 3 together with mass spectrometry characterising data (MS: APCI MH⁺). The compounds are obtained in free form, except those of Examples 34, 35, 37, 38, 39 and 43 (which are made in an analogous way to Example 3) are isolated as the free acid or as a salt, for example an alkali metal salt.

TABLE 3

| Ex. | R¹ | NR²R³ | MS |
|---|---|---|---|
| 34 | 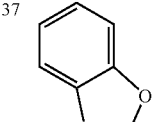 | 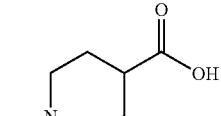 | 370.1 |
| 35 | 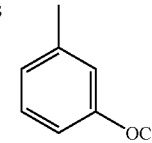 | 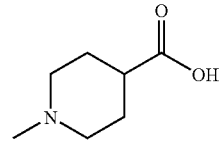 | 348.1 |
| 36 | 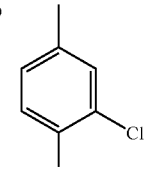 | 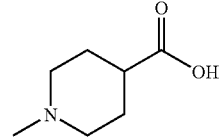 | 331.1 |
| 37 | 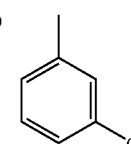 | 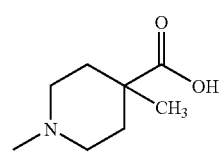 | 377.9 |
| 38 | 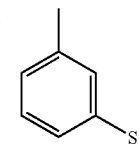 | 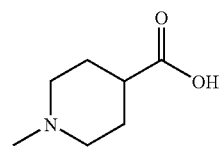 | 418.0 |
| 39 | 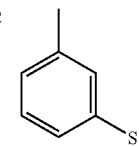 | 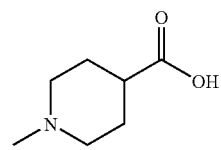 | 386.0 |
| 40 | 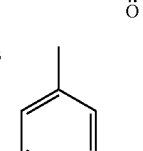 | 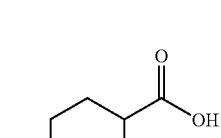 | 372.7 |
| 41 | 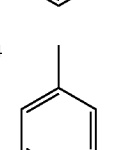 | 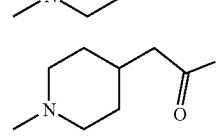 | 380.1 |
| 42 | 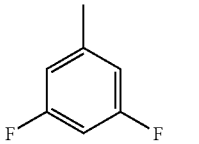 | 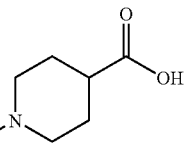 | 396.1 |
| 43 | 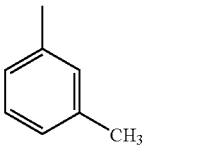 | 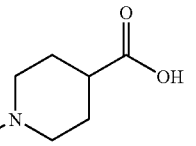 | 334.1 |
| 44 | 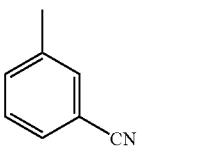 | 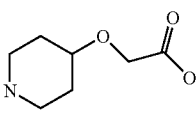 | 405.0 |

EXAMPLE 36

{1-[8-(3-Cyanophenyl)-[1,7]naphthyridin-6-yl]-piperidin-4-yloxy}-acetic acid; Potassium salt K₂CO₃ (9.5 mg, 0.070 mmol) in water (0.5 ml) is added to a solution of {1-[8-(3-cyano-phenyl)-[1,7]naphthyridin-6- yl]-piperidin4-yloxy}-acetic acid (54 mg, 0.14 mmol) in MeOH (4 ml). The reaction mixture is stirred at room temperature for 1 hour, filtered, and concentrated. The product is lyophilised from water (×3) then dried at 400° C. in vacuo for 18 hours. Trituration with ether gives the product as an amorphous solid. MS (ES+) Observed [M+H]+ 389.1601. $C_{22}H_{20}N_4O_3$ requires [M+H]+ 0389.1614

{1-[8-(3-cyano-phenyl)-[1,7]naphthyridin-6-yl]-piperidin-4-yloxy}-acetic acid

TFA (1 ml) is added to a solution of {1-[8-(3-cyano-phenyl)-[1,7]naphthyridin-6-yl]-piperidin-4-yloxy}-acetic acid tert-butyl ester (200 mg, 0.45 mmol) in $CH_2Cl_2$ (2 ml) at 0° C. The reaction mixture is stirred at 0° C. for 10 minutes then at room temperature for 1.5 hours and is then concentrated. The residue is partitioned between ethyl acetate and water and the aqueous layer is adjusted to pH 5 with 1M KOH. The aqueous layer is extracted with ethyl acetate (×3) and the combined ethyl acetate extracts are dried (MgSO4), filtered and concentrated. Purification by chromatography on silica gel, eluting with 1% MeOH in $CH_2Cl_2$ gives the product. MS (ES+) Observed [M+H]+3 89.05

{1-[8-(3-cyano-phenyl)-[1,7]naphthyridin-6-yl]-piperidin-4-yloxy}-acetic acid tert-butyl ester 3-[6-(4-Hydroxy-piperidin-1-yl)-[1,7]naphthyridin-8-yl]-benzonitrile (570 mg, 1.73 mmol) THF (5 ml) is added to NaOH (60% dispersion in mineral oil) (166 mg, 6.9 mmol) suspended in THF (20 ml) at 0° C. Stirred at 0° C. for 30 minutes. tert-Butyl bromoacetate (0.51 ml, 3.45 mmol) is added and the reaction mixture is stirred at 0° C. for 5 minutes then at room temperature for 18 hours. Further tert-butyl bromoacetate (0.25 ml, 1.73 mmol) and NaOH (80 mg, 3.3 mmol) are added and the reaction mixture is stirred at room temperature for 2 hours. After cooling to 0° C. water (20 ml) is added and the mixture is extracted with ethyl acetate (×1). The ethyl acetate extract is dried (MgSO$_4$), filtered and concentrated. Purification by chromatography on silica gel, eluting with 10-20% ethyl acetate in isohexane, gives the product. MS (ES+) Observed [M+H]+ 445.12

3-[6-(4-Hydroxy-piperidin-1-yl)-[1,7]naphthyridin-8-yl]-benzonitrile

A solution of 4-hydroxypiperidine (287 mg, 2.80 mmol) and Compound A (700 mg, 1.85 mmol) in DMSO (4 ml) is heated at 600° C. for 18 hours. On cooling, the reaction mixture is diluted with ethyl acetate (100 ml) and washed with brine (×4). The organic layer is dried (MgSO$_4$), filtered, and concentrated to give the product. MS (ES+) Observed [M+H]+ 331.05

EXAMPLE 40

1-[8-(3-Cyano-phenyl)-[1,7]naphthyridin-6-yl]-4-methyl-piperidine-4-carboxylic acid, Potassium salt To a solution of 1-[8-(3-Cyano-phenyl)-[1,7]naphthyridin-6-yl]-4-methyl-piperidine-4-carboxylic acid ethyl ester (220 mg, 0.55 mmol) in THF (2 ml) is added 1 N KOH (0.7 ml, aqueous). The reaction mixture is then stirred at 40° C. for 1.5 hours. Further 1 N KOH (0.4 ml) is added and the mixture stirred at 500° C. for four hours, then at 70° C. for 2 hours. Additional 1 N KOH (0.7 ml) is added with ethanol (4 ml) and the mixture is stirred at 45° C. for a further 18 hours. The mixture is then evaporated to dryness and the residue partitioned between water and DCM. The aqueous layer is separated and to this is added slowly 1 M HCl (aq.) until no more precipitate appears (ca. pH 3). The aqueous layer is then stirred at room temperature for 3 hours. The suspension is filtered and washed with water. After drying, this product is purified by flash column chromatography eluting with 1% methanol in DCM to yield the free acid. This product is stirred in 2:1 methanol:water (10 ml) to which is added 1 N K$_2$CO$_3$. After stirring at room temperature for 0.5 hours the solvents are removed and the residue is triturated in ethyl acetate. Filtration yields the desired product.

M.p. 132-136° C.; MS (ES+) Observed [M+H]+ 372.7

1-[8-(3-Cyano-phenyl)-[1,7]naphthyridin-6-yl]-4-methyl-piperidine-4-carboxylic acid ethyl ester To a solution of Compound A (360 mg, 0.96 mmol) in DMSO (3.5 ml) under argon is added 4-methyl-piperidine-4-carboxylic acid ethyl ester (hydrochloride salt) (500 mg, 2.4 mmol) and Hunig's base (0.42 ml, 3.6 mmol). The reaction mixture is stirred at 70° C. for 42 hours. The mixture is then allowed to cool to room temperature and partitioned between ethyl acetate and brine. The organic layer is washed twice more with brine then dried with anhydrous sodium sulfate and concentrated. Purification by flash column chromatography eluting with 9:1 isohexane:ethyl acetate yields the desired product as an amorphous solid.

MS (TOF ES+) 401.17

EXAMPLE 41

1-[8-(3-Metylsulfanyl-phenyl)-[1,7]naphthyridin-6-yl]-piperidine-4-carboxylic acid To a solution of 1-[8-(3-Methylsulfanyl-phenyl)-[1,7]naphthyridin-6-yl]-piperidine-4-carboxylic acid ethyl ester (134 mg, 0.33 mmol) in THF (1 ml) is added sodium hydroxide (0.33 ml of a 1M aqueous solution). The solution is stirred at room temperature for 23 hours and then partitioned between ethyl acetate and water. The aqueous extract is acidified with 7 M HCl to pH 4 and washed with ethyl acetate (3×). The combined organic layers are then concentrated to give the title compound as an amorphous solid. MS (TOF ES+) 380.1107

1-[8-(3-Methylsulfanyl-phenyl)-[1,7]naphthyridin-6-yl]-piperidine-4-carboxylic acid ethyl ester To a solution of trifluoro-methanesulfonic acid 8-(3-methylsulfanyl-phenyl)-[1,7]naphthyridin-6-yl ester (160 mg, 0.4 mmol) in DMSO (1 ml) is added ethyl isonipecotate (138 mg). The solution is stirred at 60° C. for 23 hours and then partitioned between ethyl acetate and water. The organic layer is separated and washed with brine 3×., then dried over magnesium sulfate and concentrated. The crude product is purified by flash chromatography on silica gel, eluting with 8% isohexane:DCM, increasing polarity to 2% methanol:DCM. The product is obtained as an amorphous solid. MS (ES+) 408.0893

Trifluoro-methanesulfonic acid 8-(3-methylsulfanyl-phenyl)-[1,7]naphthyridin-6-yl ester To a solution of 8-(3-methylsulfanyl-phenyl)-[1,7]naphthyridin-6-ylamine (2.05 g, 7.68 mmol) in DMF (30 ml) at 0°

C. is added triflic acid (20 ml) slowly. Sodium nitrite (1.06 g) is then added slowly over 15 minutes and the reaction mixture allowed to warm to room temperature. After stirring for 23 hours the reaction is complete by HPLC. The mixture is then diluted with ethyl acetate and washed with water, 2 N sodium carbonate and brine. The organic layer is dried over magnesium sulfate and concentrated. The product is purified by silica gel chromatography, eluting with 30% ethyl acetate in isohexane. The product is obtained as an amorphous solid. MS (ES+) 400.9948

8-(3-Methylsulfanyl-phenyl)-[1,7]naphthyridin-6-ylamine 8-(3-Methylsulfanyl-phenyl)-[1,7]naphthyridin-6-ylamine is prepared in an analogous manner to compound D (see Example 22) using 3-methylthiophenyl boronic acid to yield the product, MS (ES+) 268.04

EXAMPLE 42

1-[8-(3-Methanesulfinyl-phenyl)-[1,7]naphthyridin-6-yl]-piperidine-4-carboxylic acid Example 41 (1-[8-(3-Methylsulfanyl-phenyl)-[1,7]naphthyridin-6-yl]-piperidine-4-carboxylic acid) (30 mg, 0.07 mmol) is dissolved in methanol (200 µl), and hydrogen peroxide (11.1 µl) is added at room temperature. After 3 hours a further amount of hydrogen peroxide (15 µl) is added and the reaction mixture stirred at 45° C. overnight. The mixture is then cooled to room temperature, diluted with water and acidified with 7 M HCl (1 drop). The reaction mixture is extracted into ethyl acetate, which is washed with water and brine. The organic layer is then dried over magnesium sulfate and concentrated to give the product as an amorphous solid. MS (ES+) 396.1308

EXAMPLE 44

{1-[8-(3-Cyano-phenyl)-[1,7]naphthyridin-6-yl]-piperidin-4-yl}-acetic acid; Potassium salt To a stirred suspension of {1-[8-(3-Cyano-phenyl)-[1,7]naphthyridin-6-yl]-piperidin-4-yl}-acetic acid (160 mg, 0.43 mmol) in methanol (5 ml) is added a 1 M $K_2CO_3$ solution (aq., 0.215 ml, 0.43 mmol). The solution is stirred at room temperature for 5 minutes then the solvents are removed in vacuo. The residue is triturated in diethyl ether for 2 hours, then filtered and washed with diethyl ether to yield the desired product. M.p. 158-168° C.; MS (TOF ES+) 404.97

{1-[8-(3-Cyano-phenyl)-[1,7]naphthyridin-6-yl]-piperidin-4-yl}-acetic acid

{1-[8-(3-Cyano-phenyl)-[1,7]naphthyridin-6-yl]-piperidin-4-yl}-acetic acid ethyl ester (250 mg, 0.62 mmol) is dissolved in ethanol (5 ml) with 2M KOH (aq., 0.95 ml, 1.86 mmol) and the mixture stirred at 45° C. for 0.5 hours. After cooling, the pH of the mixture is adjusted to pH 3 by the dropwise addition of concentrated HCl. After stirring for 0.5 hours, the resultant solid is filtered and washed with water to yield the desired product. M.p. 178-180° C.

{1-[8-(3-Cyano-phenyl)-[1,7]naphthyridin-6-yl]-piperidin-4-yl}-acetic acid ethyl ester Compound A (500 mg, 1.32 mmol) is heated in DMSO (2.5 ml) with 4-piperidine acetic acid ethyl ester (560 mg, 3.30 mmol) and Hunig's base (0.66 ml) at 70° C. for 20 hours. The mixture is then diluted with ethyl acetate and washed with brine (3×). The organic layer is then dried over magnesium sulfate, then filtered and concentrated. Purification by flash column chromatography eluting with 6:1 isohexane: ethyl acetate yields the desired product. MS (AP+) 401.1

The invention claimed is:
1. A compound of formula I

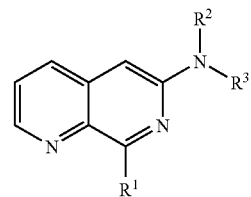

in free or salt form, where
$R^1$ is a monovalent aromatic group having up to 10 carbon atoms; and
$R^2$ and $R^3$ together with the nitrogen atom to which they are attached denote a heterocyclic group having up to 10 ring atoms and having 1 to 4 hetero atoms in the ring system.

2. A compound according to claim 1, in which
$R^1$ is phenyl substituted by one or two substituents selected from cyano, halogen, carboxy or $C_1$-$C_4$-haloalkoxy, and optionally by $C_1$-$C_4$-alkyl or $C_1$-$C_4$-alkoxy, or $R^1$ is phenyl substituted by $C_1$-$C_4$-alkoxy; and
$R^2$ and $R^3$ together with the nitrogen atom to which they are attached denote a heterocyclic group having up to 6 ring atoms and one or two hetero atoms in the ring.

3. A compound according to claim 1, in which
$R^1$ is phenyl substituted by one or two substituents selected from cyano, halogen, carboxy or $C_1$-$C_4$-haloalkoxy meta to the indicated naphthyridine ring and optionally by $C_1$-$C_4$-alkyl or $C_1$-$C_4$-alkoxy ortho to the indicated naphthyridine ring, or $R^1$ is phenyl substituted by $C_1$-$C_4$-alkoxy meta to the indicated naphthyridine ring; and
$R^2$ and $R^3$ together with the nitrogen atom to which they are attached denote a heterocyclyl group having up to 6 ring atoms and one or two nitrogen atoms, or one nitrogen atom and one oxygen atom, in the ring, optionally substituted by hydroxy, carboxy, 5-membered O-heterocyclylcarbonyl, aminocarbonyl, $C_1$-$C_4$-alkoxycarbonyl, $C_1$-$C_4$-alkylsulfonyl or $C_1$-$C_4$-alkyl optionally substituted by hydroxy, cyano, carboxy or $C_1$-$C_4$-alkoxycarbonyl.

4. A compound according to claim 1 in which
$R^1$ is phenyl optionally substituted by one, two or three substituents selected from the group consisting of cyano, $C_1$-$C_8$-alkyl, $C_1$-$C_8$-alkylthio, —SO—$C_1$-$C_8$-alkyl, and phenyl fused with a heterocyclic ring having 3 to 8 ring atoms of which up to 4 can be carbon atoms and up to 4 can be hetero atoms; and
$R^2$ and $R^3$ together with the nitrogen atom to which they are attached denote a heterocyclic group having up to 6 ring atoms and one or two hetero atoms in the ring optionally substituted by carboxy, carboxy-$C_1$-$C_8$-alkoxy or $C_1$-$C_8$-alkoxycarbonyl-$C_1$-$C_8$-alkoxy, said heterocyclic group also optionally being substituted by $C_1$-$C_8$-alkyl or $C_1$-$C_8$-alkoxy.

5. A compound according to claim 4, in which
$R^1$ is phenyl optionally substituted by one, two or three substituents selected from the group consisting of cyano, $C_1$-$C_4$-alkyl, $C_1$-$C_4$-alkylthio, —SO—$C_1$-$C_4$-alkyl, and phenyl fused with a heterocyclic ring having 5 or 6 ring atoms of which up to 4 can be carbon atoms and up to 2 can be hetero atoms; and
$R^2$ and $R^3$ together with the nitrogen atom to which they are attached denote a heterocyclic group having up to 6 ring atoms and one or two nitrogen atoms in the ring optionally substituted by carboxy, carboxy-$C_1$-$C_4$-alkoxy or $C_1$-$C_4$-alkoxycarbonyl-$C_1$-$C_4$-alkoxy, said heterocyclic group also optionally being substituted by $C_1$-$C_4$-alkyl.

6. A compound according to claim 1, which is
3-[6-(3-hydroxy-pyrrolidin-1-yl)-[1,7]naphthyridin-8-yl]-benzonitrile;
3-{6-[4-(2-cyano-ethyl)-piperazin-1-yl]-[1,7]naphthyridin-8-yl}-benzonitrile;
1-[8-(3-cyano-phenyl)-[1,7]naphthyridin-6-yl]-piperidine-4-carboxylic acid, lithium salt; or
3-(6-piperazin-1-yl-[1,7]naphthyridin-8-yl)-benzonitrile;
1-[8-(3-fluoro-phenyl)-[1,7]naphthyridin-6-yl]-piperidine-4-carboxylic acid ethyl ester;
sodium 1-[8-(3-fluoro-phenyl)-[1,7]naphthyridin-6-yl]-piperidine-4-carboxylate;
1-[8-(5-fluoro-2-methoxy-phenyl)-[1,7]naphthyridin-6-yl]-piperidine-4-carboxylic acid ethyl ester; or
potassium 1-[8-(5-fluoro-2-methoxy-phenyl)-[1,7]naphthyridin-6-yl]-piperidine-4-carboxylate.

7. A compound according to claim 1, wherein $R^1$ and —$NR^2R^3$ are as shown in the following table:

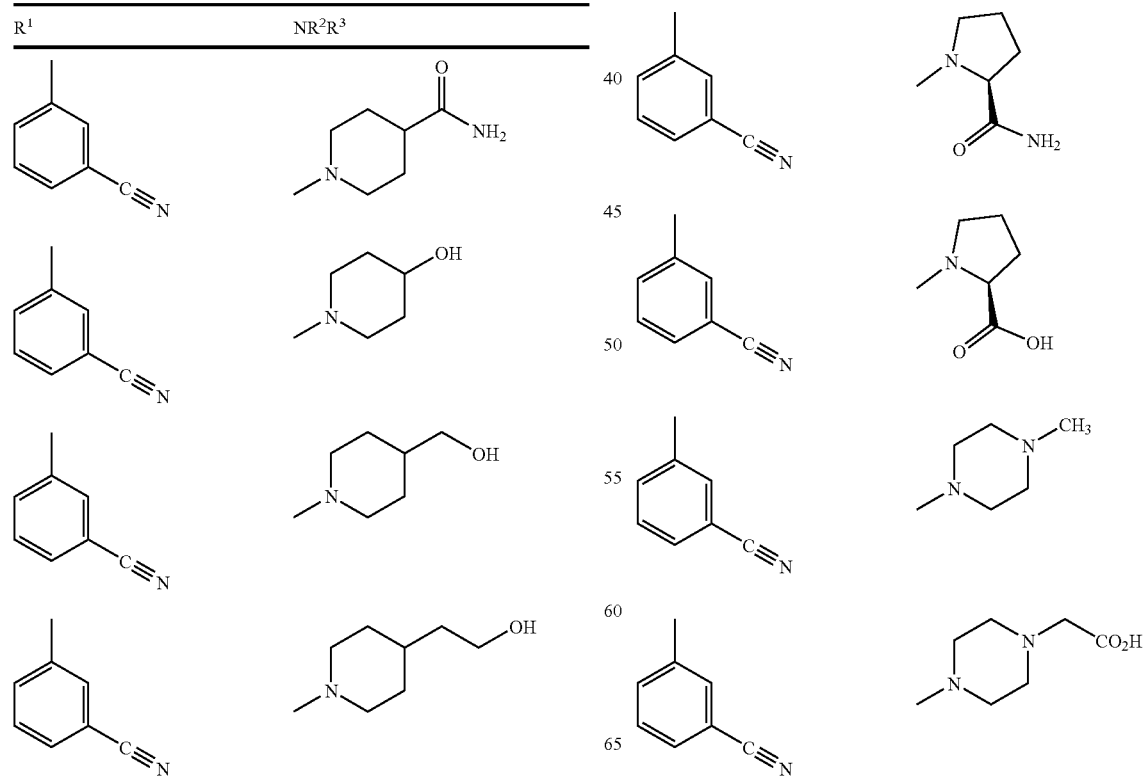
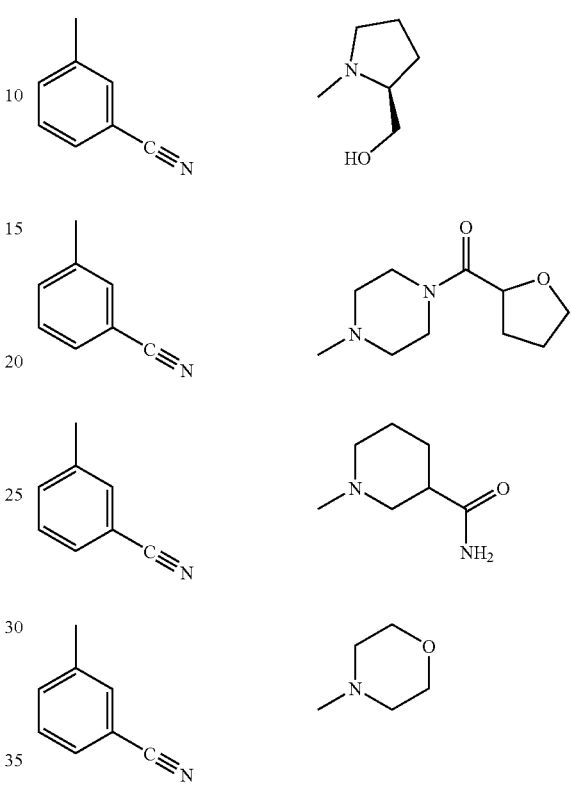

| R¹ | NR²R³ |
|---|---|
| 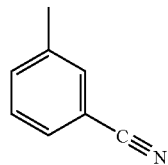 | 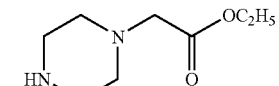 |
| 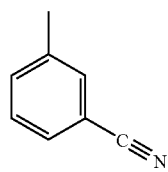 | 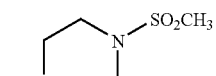 |
| 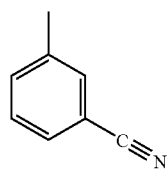 | 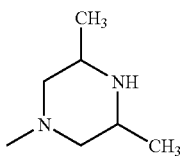 |
| 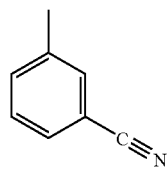 | 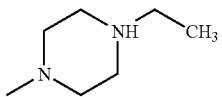 |
| 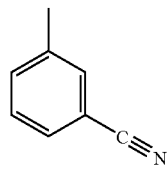 | 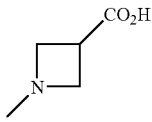 |
| 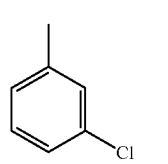 | 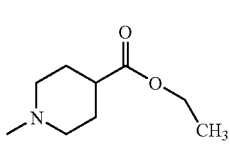 |
| 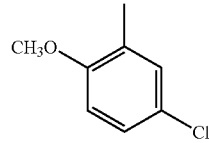 | 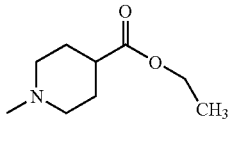 |
| 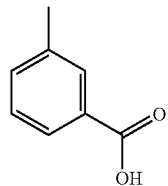 | 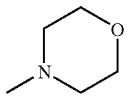 |
| 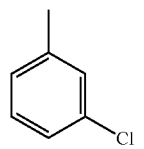 | 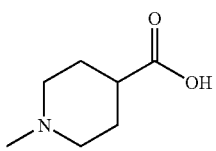 |
| R¹ | NR²R³ |
|---|---|
| 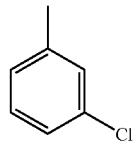 | 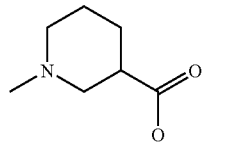 |
| 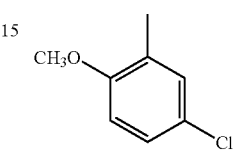 | 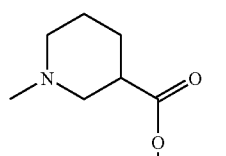 |
| 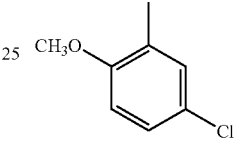 | 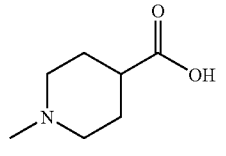 |
| 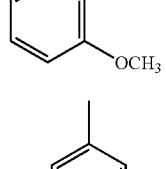 | 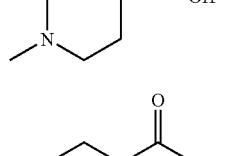 |
| 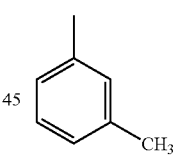 | 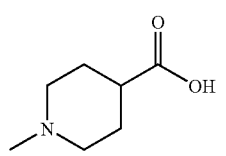 |
| 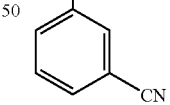 | 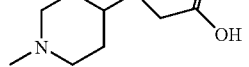 |
| 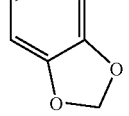 | 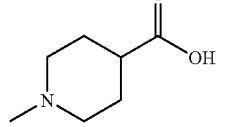 |
| 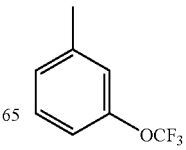 | 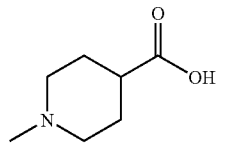 |

-continued

| R¹ | NR²R³ |
|---|---|
| 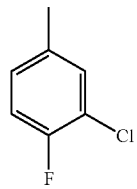 | 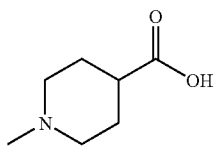 |
| 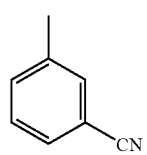 | 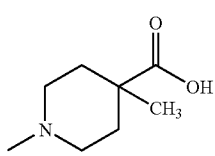 |
| 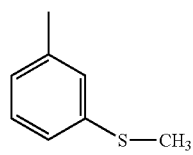 | 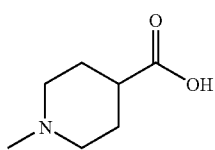 |
| 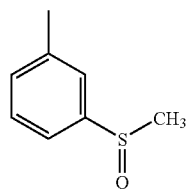 | 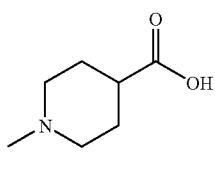 |
| 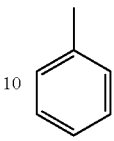 | 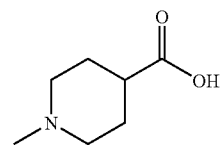 |
| 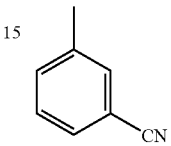 | 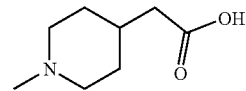 |

8. A pharmaceutical composition comprising a compound according to claim 1, optionally together with a pharmaceutically acceptable diluent or carrier.

9. A pharmaceutical composition comprising a compound according to claim 6, optionally together with a pharmaceutically acceptable diluent or carrier.

10. A pharmaceutical composition comprising a compound according to claim 7, optionally together with a pharmaceutically acceptable diluent or carrier.

* * * * *